United States Patent
Huter et al.

(12)

(10) Patent No.: US 6,599,307 B1
(45) Date of Patent: Jul. 29, 2003

(54) FILTER DEVICE FOR EMBOLIC PROTECTION SYSTEMS

(75) Inventors: Benjamin C. Huter, Murrieta, CA (US); John E. Papp, Temecula, CA (US); Anuja Patel, San Jose, CA (US); John D. Whitfield, Temedula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 10 days.

(21) Appl. No.: 09/919,503

(22) Filed: Jul. 31, 2001

Related U.S. Application Data

(63) Continuation-in-part of application No. 09/896,142, filed on Jun. 29, 2001.

(51) Int. Cl.⁷ .............................................. A61M 29/00
(52) U.S. Cl. ........................................ 606/200; 606/159
(58) Field of Search ................................ 606/200, 113, 606/114, 127, 159, 194

(56) References Cited

FOREIGN PATENT DOCUMENTS

| WO | WO 96/01591 | 1/1996 |
|----|-------------|--------|
| WO | WO 00/67670 | 11/2000 |
| WO | WO 01/10346 | 2/2001 |
| WO | WO 01/45592 | 6/2001 |
| WO | WO 01/49215 | 7/2001 |

*Primary Examiner*—Michael J. Milano
*Assistant Examiner*—Victor Nguyen
(74) *Attorney, Agent, or Firm*—Fulwider Patton Lee & Utecht, LLP

(57) ABSTRACT

A system for enabling the insertion and removal of an embolic protection device, for capturing and retaining embolic debris which may be created during the performance of a therapeutic interventional procedure in a stenosed or occluded region of a blood vessel. The system, in an embodiment thereof, enables the device to be snap-fitted so as to engage the distal end of a guide wire, to provide a reference for positioning the device at a location distal to the interventional procedure site, and to enable an end of the device to be in tension, enabling a portion of the device to be in tension and another portion to be in compression, so as to assist in bending thereof in tortuous vasculature.

21 Claims, 2 Drawing Sheets

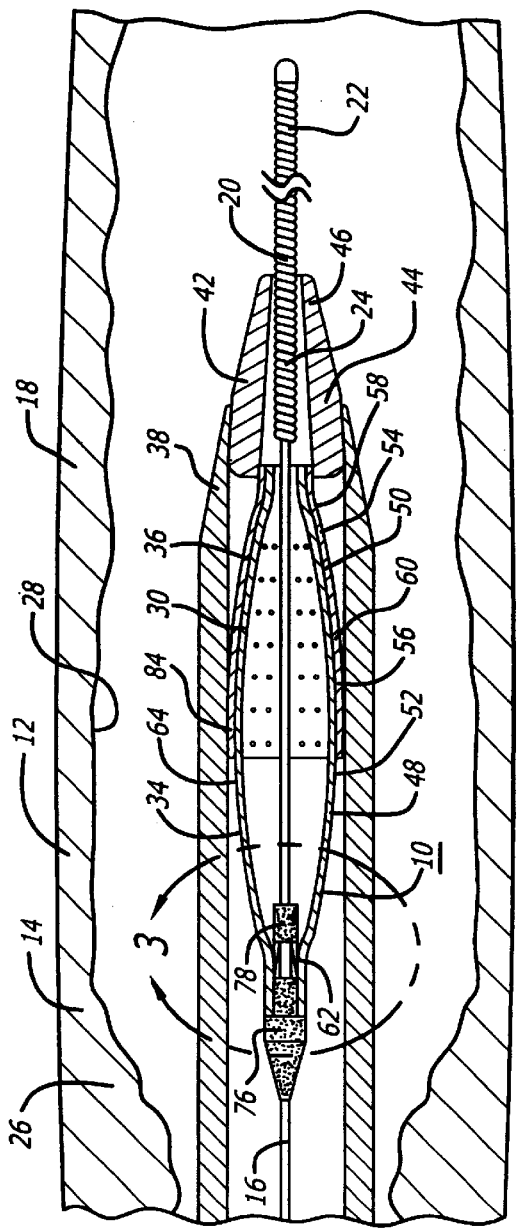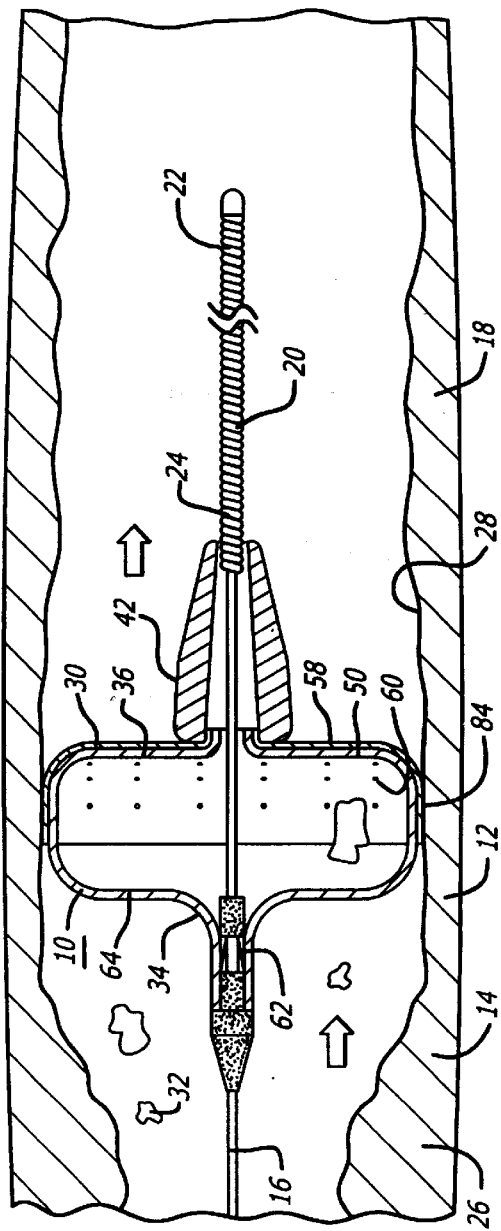

FILTER DEVICE FOR EMBOLIC PROTECTION SYSTEMS

RELATED APPLICATIONS

This application is a continuation-in-part of application Ser. No. 09/896,142 filed on Jun. 29, 2001.

BACKGROUND OF THE INVENTION

The present invention relates generally to improvements in embolic protection systems and methods. In particular, it relates to an improved system and method for enabling an embolic protection device to be efficiently and conveniently engaged with the distal end of a guide wire. The system also enables the device to effectively expand against the inner surface of a blood vessel wall, and to seal off the inner surface thereof upon deployment thereof at a location distal to an interventional procedure site. Such deployment enables the efficient capture of embolic material, which may be created and released into the bloodstream during the performance of the interventional procedure in a stenosed or occluded region of a blood vessel, and prevents embolic material from bypassing the embolic protection device. The system further enables the embolic protection device to provide a reference for the effective positioning thereof at the location distal to the interventional procedure site. It also is formed of expandable material for enabling efficient expansion thereof, and includes a portion thereof formed so as to be in tension, such that another portion thereof is in compression, to effectively assist in enabling the system to bend in tortuous vasculature.

The systems and methods of the present invention are particularly useful when performing balloon angioplasty, stenting procedures, laser angioplasty or atherectomy in critical vessels, such as the carotid, renal, and saphenous vein graft arteries, where the release of embolic debris into the bloodstream could possibly occlude the flow of oxygenated blood to the brain or other vital organs which can cause devastating consequences to the patient.

A variety of non-surgical interventional procedures have been developed over the years for opening stenosed or occluded blood vessels in a patient caused by the build up of plaque or other substances on the walls of the blood vessel. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel.

Another procedure is laser angioplasty which utilizes a laser to ablate the stenosis by super heating and vaporizing the deposited plaque. Atherectomy is yet another method of treating a stenosed blood vessel in which a cutting blade is rotated to shave the deposited plaque from the arterial wall. A vacuum catheter may be used to capture the shaved plaque or thrombus from the blood stream during this procedure.

In another widely practiced procedure, the stenosis can be treated by placing a device known as a stent into the stenosed region to hold open and sometimes expand the segment of the blood vessel or other arterial lumen. Stents are particularly useful in the treatment or repair of blood vessels after a stenosis has been compressed by percutaneous transluminal coronary angioplasty (PTCA), percutaneous transluminal angioplasty (PTA) or removal by atherectomy or other means. Stents are usually delivered in a compressed condition to the target site, and then are deployed at the target location into an expanded condition to support the vessel and help maintain it in an open position.

In the past, stents typically have fallen into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from, for example, shape memory metals or super-elastic nickel-titanium (NiTi) alloys, which will automatically expand from a compressed state when the stent is advanced out of the distal end of the delivery catheter into the body lumen. Such stents manufactured from self-expandable materials allow for phase transformations of the material to occur, contributing to the expansion and contraction of the stent.

The above non-surgical interventional procedures, when successful, avoid the necessity of major surgical operations. However, there is one common problem associated with all of these non-surgical procedures, namely, the potential release of embolic debris into the bloodstream which can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, particles are not always fully vaporized and may enter the bloodstream.

When any of the above-described procedures are performed for example in the carotid arteries, the release of emboli into the circulatory system can be extremely dangerous to the patient. Debris that is carried by the bloodstream to distal vessels of the brain may cause these cerebral vessels to occlude, resulting in a stroke, and in some cases, death. Therefore, although carotid percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system following treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such procedures in the carotid arteries a high-risk proposition.

Other techniques which have been developed to address the problem of removing embolic debris include the use of catheters with a vacuum source which provides temporary suction to remove embolic debris from the bloodstream.

However, as mentioned above, there have been complications with such systems since the vacuum catheter may not always remove all of the embolic material from the bloodstream, and a powerful suction could cause problems to the patient's vasculature.

Further techniques which have had some limited success include the placement of an embolic protection device such as a filter or trap downstream from the treatment site to capture embolic debris before it reaches the smaller blood vessels downstream. Such embolic protection devices enable the filtering of embolic debris which may be released into the bloodstream during the treatment to the vessel, and yet allow a sufficient amount of oxygenated blood to flow past the device to supply vital organs downstream from the treatment site.

However, there have been problems associated with embolic protection devices, particularly during the assembly, insertion, and deployment thereof. The device may be mounted on the guide wire in an inconvenient manner so as to be fixedly secured thereto. Also, the mounting of the device on the guide wire, such that the device is affixed to and rotatable with the guide wire, may result in the entangling of the device in a delivery sheath, upon the device being directed in the delivery sheath through the patient's anatomy to the position distal to the interventional procedure site. Further, the expansion and deployment of the embolic protection device may not result in full and complete expansion thereof, and consequently may not seal off the inner wall of the blood vessel about the entire circumference thereof, which can result in embolic material bypassing the device. The guiding, tracking, positioning and deployment of the embolic protection device in the patient's vasculature and at the location distal to the interventional procedure site for embolic protection can be difficult and formidable.

Therefore, the present invention provides improved systems and methods for treating stenosis in blood vessels which enable an embolic protection device to be efficiently assembled and to effectively navigate through a patient's vasculature for deployment at a location distal to an interventional procedure site. It also enables the device to expand so as to effectively seal off the inner surface of the blood vessel wall, to capture embolic material, and to prevent embolic material from bypassing the embolic protection device. The improved systems and methods of the present invention further enable the efficient positioning of the embolic protection device at the location distal to the interventional procedure site, to enable the effective capture of embolic material. Also, the invention is formed of expandable material in such a manner as to accommodate the effective bending, tracking, and deploying thereof. Moreover, the systems and methods are relatively easy for a physician to use, while enabling the effective delivery and recovery of a filtering system capable of removing embolic debris released into the bloodstream. The inventions disclosed herein satisfy these and other needs.

SUMMARY OF THE INVENTION

The present invention, in general, provides a system and method for enabling the insertion and removal of a filtering system for capturing and retaining embolic debris from a blood vessel. The embolic debris may be created during the performance of a therapeutic interventional procedure, such as a balloon angioplasty or stenting procedure. The filtering system prevents the embolic debris from lodging and blocking blood vessels downstream from the interventional site.

The present invention is particularly useful for enabling an interventional procedure to be performed in vital arteries, such as the carotid arteries, in which critical downstream blood vessels can become blocked with embolic debris, including the main blood vessels leading to the brain or other vital organs. As a result, the present invention provides the physician with a higher degree of confidence in the efficient operation of a filtering system for the collection and removal of embolic debris from the blood vessel when performing high-risk interventional procedures.

The present invention enables a filtering system to be deployed in the blood vessel at a location distal to the area of treatment in the interventional procedure site. It also enables the blood to pass therethrough to enable blood to flow past the filter. It further enables the blood to be filtered to capture and retain any embolic debris which may be created during the interventional procedure.

More particularly, for example, in an embodiment of the present invention, a system is provided for enabling the effective assembly thereof for engagement with a guide wire. The present invention also enables the system to expand against the inner surface of a wall of a blood vessel so as to efficiently seal off the inner surface thereof, for enabling the capture of embolic material which may be released into the blood vessel during the therapeutic interventional procedure. Further, the system enables navigation thereof through a patient's blood vessel, including tortuous vasculature, to a position distal to an interventional procedure site, for deployment of the embolic protection device.

The system includes a guide wire, including a distal end, which is positionable within the blood vessel so as to extend to a position distal to an interventional procedure site. The system also includes a filter device, which is snap-fittable so as to engage the distal end of the guide wire, for effective and convenient engagement therewith. Elements of the filter device which enable the filter device to be snap-fitted to the guide wire are comprised of radiopaque material, for providing a reference for positioning the filter device in the patient's vasculature. The filter device is comprised of expandable material, and is formed so that an end thereof is in tension, and another portion is in compression, to aid in the bending of the filter device in tortuous vasculature.

The above objects and advantages of the present invention, as well as others, are described in greater detail in the following description, when taken in conjunction with the accompanying drawings of illustrative embodiments.

BRIEF DESCRIPTION OF THE DRAWINGS

FIG. 1 is an elevational fragmentary partly-sectional view of an embodiment of the present invention, disposed within the internal carotid artery of a patient, including a delivery sheath and an unexpanded filter device.

FIG. 2 is a similar view of the embodiment shown in FIG. 1, wherein the delivery sheath has been removed and the filter device has expanded.

DETAILED DESCRIPTION OF THE PREFERRED EMBODIMENTS

Figure 3:
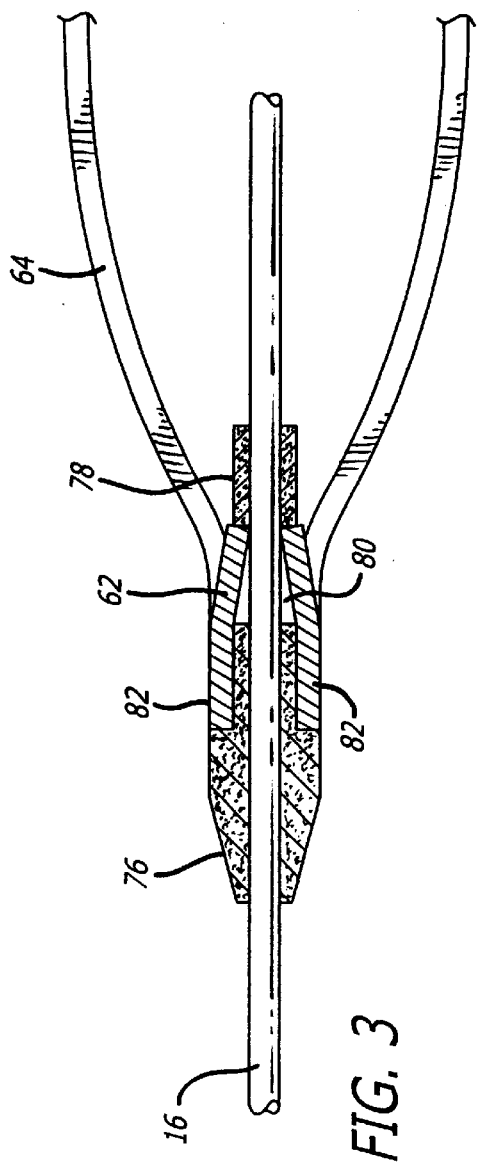
FIG. 3 is a partly cross-sectional view taken along the line 3—3 of FIG. 1.

The present invention is directed to an improved system and method for enabling the capture of embolic material which may be released into the blood vessel during the therapeutic interventional procedure, in an efficient and effective manner. The invention enables a filter device to be snap-fitted to a guide wire for effective and convenient engagement therewith, enables rotational movement of the filter device independent of rotational movement of the guide wire, and inhibits translational movement of the filter device along the guide wire. The present invention is further directed to efficiently providing a reference for positioning the filter device in the patient's anatomy. The filter device is also formed of expandable material, and includes an end thereof which is formed so as to be in tension, enabling a portion of the filter device to be in tension and another portion to be in compression, to aid the filter device in the bending thereof in tortuous vasculature.

The embodiments of the improved system and method are illustrated and described herein by way of example only and not by way of limitation. While the present invention is described as applied to the carotid arteries of the patient, those skilled in the art will appreciate that it can also be used in other body lumens as well, such as the coronary arteries, renal arteries, saphenous vein grafts and other peripheral arteries. Additionally, the present invention can be utilized when performing any one of a number of interventional procedures, such as stenting, balloon angioplasty, laser angioplasty or atherectomy.

In the drawings, wherein like reference numerals denote like or corresponding parts throughout the drawing figures, and particularly in the embodiments in accordance with the invention as shown in FIGS. 1–4, for example, a system 10 is provided for enabling an interventional procedure to be performed in a blood vessel 12 at an area of treatment 14. The system 10 is atraumatic, to inhibit injury to the patient. It includes a guide wire 16 which enables the system 10 to be positioned distal to the area of treatment 14. The system 10 is placed within the carotid artery 18 or other blood vessel of the patient, and is guided into position by the guide wire 16. The guide wire 16 includes a tip coil 20 at a distal end 22 thereof. The tip coil includes a proximal end 24. The carotid artery 18 has the area of treatment 14 therein, which comprises the interventional procedure site, wherein atherosclerotic plaque 26 has built up against the inside wall 28, which decreases the diameter of the carotid artery 18. As a result, blood flow is diminished through this area.

The therapeutic interventional procedure comprises implanting an expandable interventional instrument at the interventional procedure site 14, to press the build-up of plaque 26 of the stenosis against the inside wall 28, to increase the diameter of the occluded area 14 of the artery 18, and to help restore sufficient flow of blood to the downstream vessels leading to the brain. The expandable interventional instrument not only helps increase the diameter of the occluded area, but helps prevent restenosis in the area of treatment 14. The interventional instrument is expandable upon deployment thereof at the interventional procedure site 14.

The system 10 of the present invention enables the delivery of a filter device 30 to a location distal to the area of treatment 14, to enable deployment of the filter device 30 at the location distal to the area of treatment 14, and to enable the removal of the filter device 30 from the delivered and deployed position thereof. The filter device 30 filters the blood in the blood vessel 12, so as to pass blood therethrough and capture embolic material 32 which may be released in the blood vessel 12 during the interventional procedure. It engages the distal end 22 of the guide wire 16, so as to enable the filter device 30 to be placed within the carotid artery 18 or other blood vessel of the patient and guided into position distal to the area of treatment 14. The filter device 30 includes a proximal portion 34 and a distal portion 36.

Referring to FIGS. 1–4, in an embodiment pursuant to the present invention, for example, the system 10 enables movement thereof through the patient's blood vessel 12 to a position distal to the area of treatment 14 for deployment of the filter device 30. The system 10 further enables expansion of the filter device 30 against the inside wall 28 of the blood vessel 12 and the sealing off of the inside wall 28, to enable the capture of embolic material 32 which may be released into the blood vessel 12 during the therapeutic interventional procedure.

As illustrated in FIGS. 1–3, the system 10 in accordance with the embodiment of the invention includes the guide wire 16, positionable within the blood vessel 12, and extendable to a position distal to the interventional procedure site 14. The system 10 further includes the filter device 30, which is snap-fitted for engagement with the distal end 22 of the guide wire 16. The filter device 30 extends within a delivery sheath 38 for delivery to the interventional procedure site 14. The delivery sheath 38 includes a distal portion 40. The system 10 further includes an obturator 42, which includes a proximal end 44 and a distal end 46. The obturator 42 extends between the delivery sheath 38 and the tip coil 20, such that the distal end 46 of the obturator 42 extends along the proximal end 24 of the tip coil 20, and the proximal end 44 of the obturator 42 is substantially abutted by the distal portion 40 of the delivery sheath 38 when the delivery sheath 38 is extended over the filter device 30. The obturator 42 provides a smooth transition between the delivery sheath 38 and the tip coil 20, so as to slide smoothly around tortuous anatomy in the blood vessel 12, and to inhibit digging into, scraping, or damaging the inside wall 28 of the blood vessel 12 thereby.

The filter device 30 is deployed at the location in the patient's blood vessel 12 distal to the area of treatment 14, upon withdrawal of the delivery sheath 38. It captures embolic material 32 which may be released into the blood in the blood vessel 12 during the interventional procedure. Upon being snap-fitted onto the distal end 22 of the guide wire 16, the filter device 30 engages the guide wire 16, and enables rotation of the filter device 30 independent of rotation of the guide wire 16, while inhibiting translation thereof along the guide wire 16.

A cage 48 is included in the filter device 30. The cage 48 is snap-fitted onto the distal end 22 of the guide wire 16 for engagement therewith, and filter material 50, for filtering embolic material 32, is secured to the cage 48. The cage 48 includes a proximal portion 56 and a distal portion 58, and the filter material 50 includes a proximal end 52, a distal end 54, and a plurality of holes 60 therein for filtering embolic material 32. The proximal end 56 of the filter material 50 is secured to the cage 48, and the proximal end 44 of the obturator 42 extends over the distal portion 58 of the filter material 50.

The cage 48 further includes an engaging element 62, located at the proximal portion 52 thereof, as shown in enlarged view in FIG. 3, for enabling the cage 48 to snap-fit so as to engage the distal end 22 of the guide wire 16. The engaging element 62 enables the cage 48 to be snap-fitted onto the distal end 22 of the guide wire 16. The cage 48, upon being snap-fitted onto the distal end 22 of the guide wire 16, enables rotational movement of the cage 48 independent of rotational movement of the guide wire 16, and inhibits translational movement of the cage 48 along the guide wire 16. The cage 48 further includes a plurality of struts 64.

Figure 4:
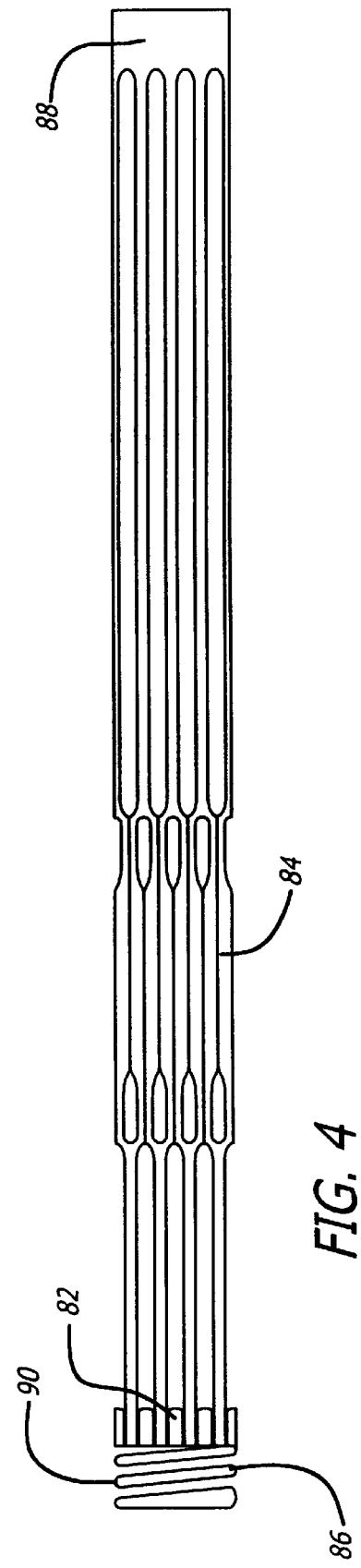
FIG. 4 is a plan view of a flattened rolled out form of a tube of material for forming the filter device, in the embodiment of the invention.

In the filter device 30, as shown in FIG. 4, the plurality of struts 64 of the cage 48 comprise a plurality of proximal ribs 66, a plurality of distal ribs 68, and a ring 70, which extends intermediate the plurality of proximal ribs 66 and the plurality of distal ribs 68. The ring 70, for example, includes a plurality of segments 72 and 74, and each adjacent pair of the plurality of segments 72 and 74 is expandable to form a generally v-shaped section of the ring 70, to seal off the inside all 28 of the blood vessel 12, so as to inhibit the formation of a gap between the cage 48 and the blood vessel inside wall 18 through which embolic material 32 may otherwise flow.

As seen in FIGS. 1–3, the system 10 further includes a proximal stop 76 and a distal stop 78, to be secured to the distal end 22 of the guide wire 16, and having a space 80 between the proximal stop 76 and the distal stop 78. The proximal stop 76 and the distal stop 78 comprise a pair of bushings, which are comprised of radiopaque material, to provide a reference for the operator of the system 10 to position the filter device 30 in the patient's blood vessel 12. The engaging element 62 of the cage 48 enables the cage 48 to be snap-fitted to the proximal stop 76 and the distal stop 78 in the space 80 therebetween. The engaging element 62 includes at least one tab 82, which is pre-bent inwardly, for example, for flexing and engaging the proximal stop 76 and the distal stop 78 in the space 80 between the proximal stop 76 and the distal stop 78. The inner diameter of the filter device 30 is at least slightly larger than the outer diameter of the tip coil 20, enabling the filter device 30 to be snap-fitted from the distal end 22 of the guide wire 16. The inner diameter of the tabs 82, for example, are at least slightly larger than the outer diameter of the distal stop 78, for enabling the filter device 30 to slide thereover, and the tabs 82 to snap-fit into position in the space 80 so as to bear against the distal stop 78. Alternatively, for example, the locations of the proximal stop 76 and the distal stop 78 could be reversed, whereby the cage 48 may be snap-fitted from a proximal end of the guide wire 16. The snap-fitted engaging element 62 inhibits translational movement of the filter device 30 relative to the guide wire 16, while enabling rotational movement of the filter device 30 independent of rotational movement of the guide wire 16.

The cage 48 of the filter device 30, as depicted in FIG. 4, may be formed from a hypotube 84 of expandable material. The hypotube 84 includes a pair of ends 86 and 88. The system 10 further includes a spring 90, connected to the end 86 of the hypotube 84, such that a portion of the cage 48 formed by the hypotube 84 is in tension, and another portion is in compression, to aid the cage 48 in the bending thereof in tortuous vasculature. The tabs 82 are formed at the end 86 of the hypotube 84 to which the spring 90 is connected.

Referring to FIGS. 1–4, in a method for the use of the embodiment in accordance with the present invention, for example, the system 10 enables movement thereof through the patient's blood vessel 12 to the location distal to the area of treatment 14 for deployment of the filter device 30, and seals off the inside wall 28 of the blood vessel 12 to enable the capture of embolic material 32. The filter device 30 and the obturator 42 are assembled, and the proximal stop 76 and the distal stop 78, which comprise a pair of bushings, are mounted on the guide wire with the space 80 therebetween. The inner diameter of the filter device 30, for example, is at least slightly larger than the outer diameter of the tip coil 20, and the at least one tab 82 is pivotable, so as to enable the filter device 30 to be inserted over the tip coil 20. The assembly of the filter device 30 and the obturator 42, for example, is inserted over the tip coil 20 to the position where the tabs 82 snap-fit into the space 80 between the pair of bushings comprising the proximal stop 76 and the distal stop 78 mounted on the guide wire 16, so as to snap-fit the filter device 30 to the distal end 22 of the guide wire 16, for efficient engagement therewith. The delivery sheath 38 is extended over the guide wire 16 so as to enclose the filter device 30 therein, and such that the distal portion 40 of the delivery sheath 38 substantially abuts the proximal end 44 of the obturator 42.

The system 10 is positioned in the patient's vasculature 12 utilizing any one of a number of different methods. In one preferred method of positioning the system 10, the delivery sheath 38, with the filter device 30 therein, is inserted into and extended through the patient's vasculature 12, to cross the stenosis in the blood vessel 12, so as to extend to a position distal to the interventional procedure site 14. The radiopaque proximal stop 76 and distal stop 78 of the engaging element 62 provide a reference for enabling the operator to accurately position the filter device 30 in the patient's vasculature 12. As seen in FIG. 4, the spring 90, connected to the end 86 of the hypotube 84 of expandable material at which the tabs 82 are formed, causes such portion of the cage 48 formed by the hypotube 84 to be in tension, and another portion to be in compression, aiding the cage 48 in the bending thereof in tortuous vasculature.

The guide wire 16 is rotatable during insertion thereof through the patient's vasculature 12, to enable guiding and directing thereof. The snap-fitted filter device 30 is rotatable on the guide wire 16 independent of rotation of the guide wire 16, during insertion of the filter device 30 through the patient's anatomy 12, to inhibit entanglement thereof, while the filter device 30 is also inhibited from translational movement thereof. The delivery sheath 38 is then withdrawn, enabling the filter device 30 to deploy so as to capture embolic material 32 which may be released in the blood vessel 12 during the interventional procedure.

After the delivery sheath 38 is withdrawn, the filter device 30, snap-fitted to the guide wire 16 at the proximal portion 52 of the cage 48 such that the tabs 82 extend between the proximal stop 76 and the distal stop 78, is released from being enclosed in the delivery sheath 38. The filter device 30 then expands and bears against the inside wall 28 of the blood vessel 12. The expansion of the filter device 30 so as to press against the inside wall 28 of the blood vessel 12 seals off the inside wall 28 of the blood vessel 12, and inhibits the formation of a gap between the filter device 30 and the blood vessel wall 28, through which embolic material 32 may otherwise flow. The filter material 50 expands with the flow of blood in the blood vessel 12 therethrough, to capture embolic material 32 which may be released during the interventional procedure.

In accordance with the present invention, the particular embodiments set forth above of the system 10 for filtering embolic material are capable of being positioned in a blood vessel. However, other forms of the system 10 may be utilized with the present invention without departing from the spirit and scope of the invention. For example, the system 10 may be comprised of other forms of material. Additionally, while the system 10 is shown as in various shapes in the embodiments herein, it can be formed in any one of a number of different shapes depending upon the construction desired.

Further, the various components may be joined by suitable adhesives such as acrylonitrile based adhesives or cyanoacrylate based adhesives. Heat shrinking or heat bonding may also be employed where appropriate. Plastic-to-plastic or plastic-to-metal joints can be effected by a suitable acrylonitrile or cyanoacrylate adhesive. Variations can be made in the composition of the materials to vary properties as needed. Based on the present disclosure, other adhesives and applications are known to one skilled in the art.

In view of the above, it is apparent that the system and method of the embodiment of the present invention enhances substantially the effectiveness of performing interventional procedures by providing a filter device for filtering embolic material, to be snap-fitted for engagement with a guide wire, and independently rotatable relative to the guide wire, for efficient assembly, insertion and removal thereof. The system and method further enable the filter device to expand against the inner wall of a blood vessel so as to seal off the inner surface thereof, to inhibit gap formation and the passing of embolic material therethrough. The system and method also include a pair of radiopaque bushings for enabling snap-fitting engagement of the filter device with the guide wire, which provide references for the positioning of the filter device in the patient's vasculature. The filter device of the system and method is formed of expandable material including a portion thereof in tension, and another portion in compression, for aiding the filter device in bending thereof in tortuous vasculature. filter device in the patient's vasculature. The filter device of the system and method is formed of expandable material including a portion thereof in tension, for aiding in tracking and deploying the filter device.

While the present invention has been described in connection with the specific embodiments identified herein, it will be apparent to those skilled in the art that many alternatives, modifications and variations are possible in light of the above description. Accordingly, the invention is intended to embrace all such alternatives, modifications and variations as may fall within the spirit and scope of the invention disclosed herein.

What is claimed:

1. A system for enabling the capture of embolic material which may be released into a blood vessel during a therapeutic interventional procedure, comprising:
    a guide wire, including a distal end, adapted to be positioned within the blood vessel and to extend to a position distal to an interventional procedure site; and
    a filter device, adapted to be positioned and deployed at a location in the patient's vasculature distal to the interventional procedure site, and to capture embolic material which may be released into the blood in the blood vessel during the interventional procedure, including an engaging element;
    wherein the guide wire further includes engageable elements, adapted to enable engagement therewith of the engaging element of the filter device, so as to enable rotational movement of the filter device independent of rotational movement of the guide wire.

2. The system of claim 1, wherein the filter device, upon engagement of the engaging element thereof with the engageable elements of the guide wire, is further adapted to inhibit translational movement of the filter device relative to the guide wire.

3. The system of claim 1, wherein the engageable elements in the guide wire include a proximal stop and a distal stop, adapted to be secured to the distal end of the guide wire, and having a space between the proximal stop and the distal stop, and adapted to enable the engaging element of the filter device to be engaged with the proximal stop and the distal stop in the space between the proximal stop and the distal stop.

4. The system of claim 1, wherein the filter device includes a cage, adapted to be engaged with the distal end of the guide wire, and filter material, for filtering embolic material, secured to the cage.

5. The system of claim 1, wherein the guide wire includes a tip coil, at the distal end of the guide wire, the tip coil includes a proximal portion, and the system further comprises an obturator, which includes a distal portion, wherein the distal portion of the obturator is adapted to extend over the proximal portion of the tip coil.

6. The system of claim 1, wherein the filter device is adapted to be formed from a hypotube of expandable material.

7. The system of claim 3, wherein the proximal stop and the distal stop comprise a pair of bushings.

8. The system of claim 3, wherein the engaging element of the filter device comprises at least one tab, adapted to engage the proximal stop and the distal stop in the space between the proximal stop and the distal stop.

9. The system of claim 4, wherein the cage includes a plurality of struts.

10. The system of claim 4, wherein the cage includes a proximal end, and the engaging element is located at the proximal end of the cage.

11. The system of claim 5, wherein the cage includes a distal end, the obturator further includes a proximal portion, and the proximal portion of the obturator is adapted to extend over the distal portion of the cage.

12. The system of claim 5, wherein the filter device includes a cage, adapted to be snap-fitted onto the distal end of the guide wire, and filter material, for filtering embolic material, and the filter material includes a proximal end, secured to the cage, and a distal portion, and the proximal portion of the obturator extends over the distal portion of the filter material.

13. The system of claim 6, wherein the hypotube includes a plurality of ends, and the system further comprises a spring, adapted to be connected to an end of the hypotube, to enable a portion of the cage, to be formed from the hypotube by the system, to be in tension, and another portion thereof to be in compression, so as to aid the cage in the bending thereof through tortuous vasculature.

14. The system of claim 13, wherein the hypotube includes at least one tab, formed at the end thereof at which the spring is adapted to be connected and which is adapted to be in tension.

15. A method of enabling the capture of embolic material which may be released into a blood vessel during a therapeutic interventional procedure, in a system which comprises a guide wire, including a distal end, adapted to be positioned within the blood vessel and to extend to a position distal to an interventional procedure site, and a filter device, adapted to be positioned and deployed at a location in the patient's vasculature distal to the interventional procedure site, and to capture embolic material which may be released into the blood in the blood vessel during the interventional procedure, including an engaging element, wherein the guide wire further includes engageable elements, adapted to enable engagement therewith of the engaging element of the filter device, so as to enable rotational movement of the filter device independent of rotational movement of the guide wire, wherein the method comprises:

engaging the engaging element of the filter device with the engageable elements of the guide wire so as to enable rotational movement of the filter device independent of rotational movement of the guide wire;

inserting the filter device and the guide wire to the location in the patient's vasculature distal to the interventional procedure site; and expanding the filter device for deployment thereof.

16. The method of claim 15, wherein the system further includes a proximal stop and a distal stop, comprising a pair of bushings adapted to be secured to the distal end of the guide wire, and having a space between the proximal stop and distal stop, and adapted to enable the engaging element of the filter device to be engaged with the proximal stop and the distal stop in the space between the proximal stop and the distal stop, and the engaging element of the filter device comprises at least one tab, and wherein snap-fitting comprises engaging the at least one tab in the space between the pair of bushings.

17. The method of claim 15, wherein the filter device is adapted to be formed from a hypotube of expandable material, the hypotube includes a plurality of ends and at least one tab formed at an end thereof, and the system further comprises a spring, adapted to be connected to the tab end of the hypotube at which the at least one tab is formed, to enable a portion of the cage, to be formed from the hypotube by the system, to be in tension, and another portion thereof to be in compression, so as to aid the cage in the bending thereof through tortuous vasculature, further comprising forming the filter device from the hypotube, forming the at least one tab at the tab end of the hypotube, and connecting the spring to the tab end of the hypotube such that the tab end of the hypotube is in tension.

18. The system of claim 1, wherein the engageable elements are adapted to enable snap-fitted engagement of the engaging element of the filter device.

19. The system of claim 1, wherein the engageable elements are comprised of radiopaque material, for providing a reference for positioning the filter device in the patient's vasculature.

20. The method of claim 15, wherein the engageable elements are adapted to enable snap-fitted engagement of the engaging element of the filter device, and wherein engaging further comprises snap-fitted engaging of the engaging element of the filter device with the engageable elements of the guide wire.

21. The method of claim 15, wherein the engageable elements are comprised of radiopaque material, for providing a reference for positioning the filter device in the patient's vasculature, and wherein inserting further comprises inserting the filter device and the guide wire such that the radiopaque engaging element provides a reference for positioning the filter device.

* * * * *

UNITED STATES PATENT AND TRADEMARK OFFICE
CERTIFICATE OF CORRECTION

PATENT NO. : 6,599,307 B1  Page 1 of 1
DATED : July 29, 2003
INVENTOR(S) : Benjamin C. Huter et al.

It is certified that error appears in the above-identified patent and that said Letters Patent is hereby corrected as shown below:

Title page,
Item [75], Inventors, change "Temedula" to read -- Temecula --.
Item [56], References Cited, add the following:
-- U.S. PATENT DOCUMENTS
4,832,055    5/1989    Palestrant,
5,201,757    4/1993    Heyn et al.,
6,336,934    1/2002    Gilson et al.,
6,391,044    5/2002    Yadav et al. --.

Column 9,
Line 34, after "tension", add -- and another portion in compression --.
Line 34, after "aiding", delete "in tracking and deploying".
Line 35, after "device", but before ".", add -- in bending thereof in tortuous vasculature --.

Signed and Sealed this

Thirtieth Day of March, 2004

JON W. DUDAS
*Acting Director of the United States Patent and Trademark Office*